United States Patent [19]

Rice et al.

[11] Patent Number: 4,866,992

[45] Date of Patent: Sep. 19, 1989

[54] DEVICE AND METHOD FOR TENSILE TESTING OF BRITTLE MATERIALS

[76] Inventors: Edward K. Rice, 2077 Linda Flora Dr., Los Angeles, Calif. 90077; Hassan Kunbargi, P.O. Box 241472, Los Angeles, Calif. 90024

[21] Appl. No.: 19,876

[22] Filed: Feb. 27, 1987

[51] Int. Cl.$^4$ .............................................. G01N 3/02
[52] U.S. Cl. ....................................... 73/856; 73/831
[58] Field of Search ................ 73/856, 857, 858, 859, 73/860, 831, 833, 827, 828, 830; 403/221; 156/293; 24/122.3, 122.6

[56] References Cited

U.S. PATENT DOCUMENTS

| | | |
|---|---|---|
| 2,608,857 | 9/1952 | La Torre et al. ................. 73/828 X |
| 3,107,523 | 10/1963 | Oliver, Jr. et al. ............... 73/828 X |
| 3,246,671 | 4/1966 | Stein et al. ...................... 156/293 X |

*Primary Examiner*—Jerry W. Myracle
*Attorney, Agent, or Firm*—Lyon & Lyon

[57] ABSTRACT

An apparatus and method for testing brittle materials in tension includes a gripping sleeve of a viscous yieldable material placed over a specimen and a pulling sleeve adapted for placement over the gripping sleeve and for attachment to a testing apparatus. The pulling sleeve imparts load to the gripping sleeve which in turn imparts load to the specimen. Elements are provided to minimize elastic rebound.

15 Claims, 3 Drawing Sheets

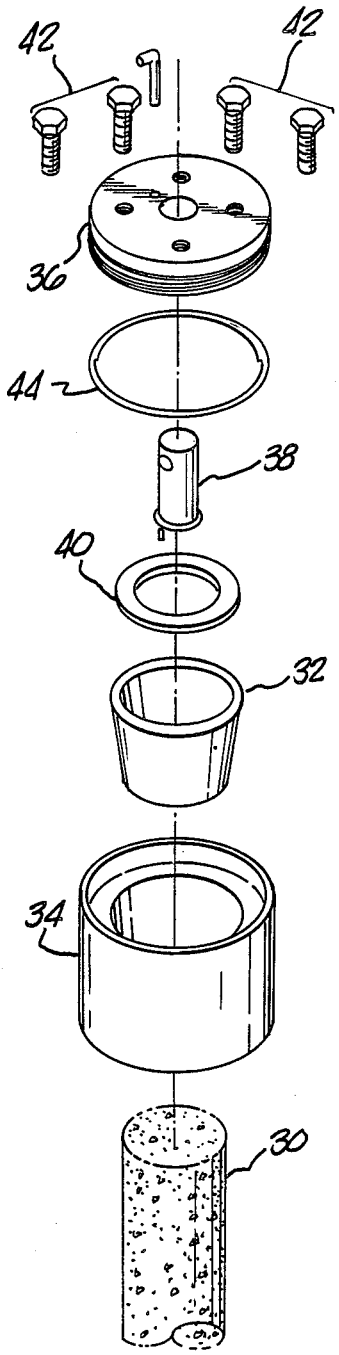
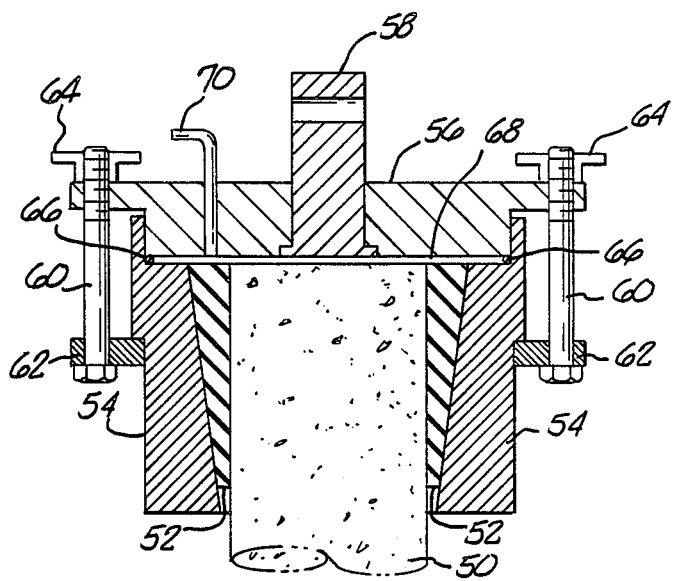
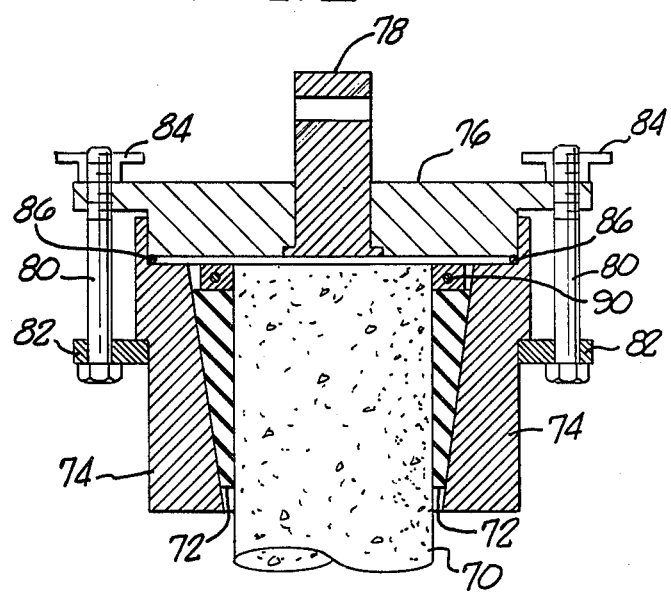

DEVICE AND METHOD FOR TENSILE TESTING OF BRITTLE MATERIALS

BACKGROUND

The field of the present invention is the testing of brittle materials in tension, and more particularly, the application of uniaxial tensile loads to brittle materials to determine tensile strength Tensile testing of brittle materials such as cement and concrete has been an unsolved problem for some time, as evidenced by the fact that in 1968, ASTM Specifications for tensile testing of cement mortar specimens (ASTM C190) were discontinued due to lack of reproducible test results.

Difficulties associated with the testing of brittle materials in tension stem from several sources. The apparatus for gripping the typically cylindrical test specimen may cause a fracture in the "grip" due to stress risers such as teeth, etc. Localized failure may also result from lack of axial alignment of the specimen. If either of these conditions are present, the specimen can fail prematurely and accurate results will not be obtained. A second area of concern is elastic rebound caused by the release of energy when a matrix material such as concrete fractures in tension. Rebound will introduce a shock load in the remaining material causing it to break at a load lower than its real tensile value.

Accordingly, a device and method for the tensile testing of brittle material that overcomes these problems would be desirable.

SUMMARY

The present invention is directed to a device and method for testing brittle materials under uniaxial tensile load. To this end, a gripping device is employed which includes a griping sleeve of a viscous yieldable material and a pulling sleeve configured to impart load to the gripping sleeve. The pulling sleeve is adapted for attachment to a loading apparatus such as a test machine. Means are provided for mimimizing elastic rebound.

BRIEF DESCRIPTION OF THE DRAWINGS

FIG. 4 is an exploded perspected view of the apparatus of FIG. 3 showing the constituent elements prior to assembly.

FIG. 5 is a sectional view of another apparatus for gripping a specimen, shown in the assembled state.

FIG. 7 is a sectional view of another apparatus for gripping a specimen in the assembled state.

DETAILED DESCRIPTION OF PREFERRED EMBODIMENTS

Figure 1:
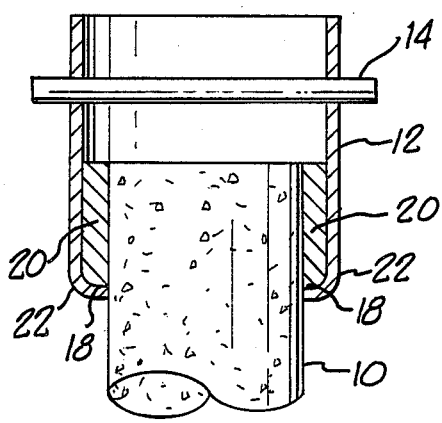
FIG. 1 is a sectional view of an apparatus for gripping a specimen of brittle material, shown in the assembled state.
Figure 2:
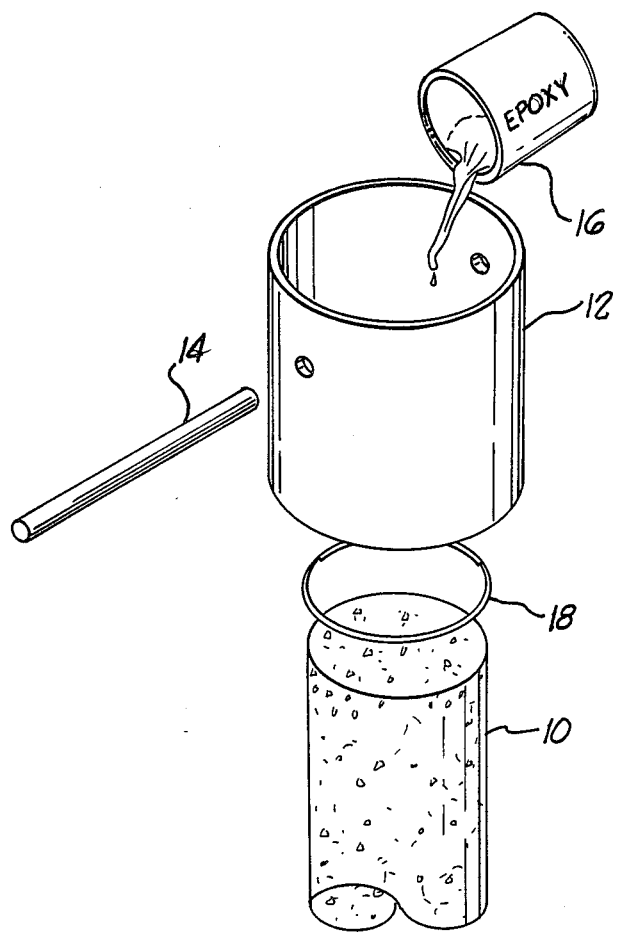
FIG. 2 is an exploded perspective view of the apparatus of FIG. 1 showing the constituent elements prior to assembly.

Turning now to the Figures, FIGS. 1 and 2 show an apparatus for gripping a specimen of brittle material 10 such as, but not limited to, a cylinder of concrete. The apparatus comprises a pulling sleeve 12 which is adapted for attachment to a conventional tension loading apparatus (not shown) via a pin member 14. A gripping sleeve 20 of a viscous yieldable material, in this case epoxy 16, is formed over the specimen 10 using the pulling sleeve 12 as a mold. An "O" ring 18 of resilient material is positioned inside the pulling sleeve 12, around the specimen 10, to prevent epoxy from escaping therefrom. As the epoxy hardens a strong bond will be formed by the gripping sleeve 20 of epoxy between the specimen 10 and the pulling sleeve 12. A lip 22 on the pulling sleeve 12 engages the gripping sleeve 20 to assist in imparting load to the gripping sleeve. The gripping sleeve 20 in turn imparts load to the specimen 10 via the epoxy bond therebetween.

Figure 3:
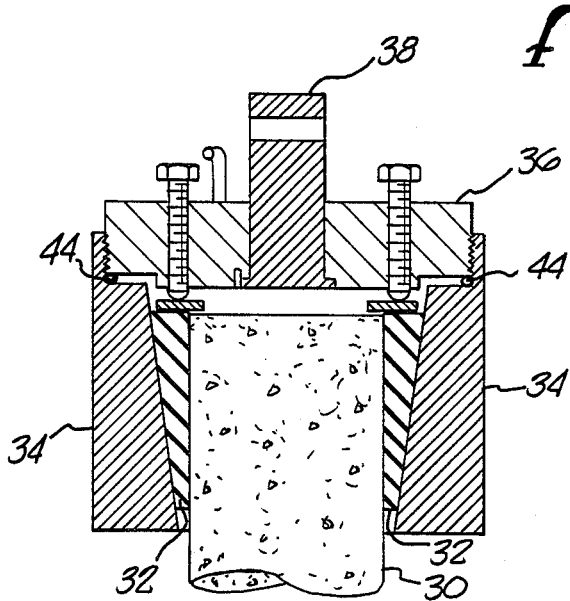
FIG. 3 is a sectional view of another apparatus for gripping a specimen, shown in the assembled state.

FIGS. 3 and 4 illustrate an apparatus for gripping a specimen 30. The apparatus comprises a gripping sleeve 32 of a viscous yieldable material, in this case neoprene. The gripping sleeve 32 is ring-shaped, and has a cylindrical inner surface adapted to fit snuggly over the cylindrical outer surface of the specimen 30, and a tapered outer surface of frustoconical shape. The gripping sleeve 32 is placed over the specimen 30 such that the frustoconical apex of the outer surface of the gripping sleeve 32 is oriented toward the longitudinal midpoint or center of the specimen 30. A pulling sleeve 34 is placed over the gripping sleeve 32. The pulling sleeve 34 is made from aluminum, although other materials could also be used, and is configured on its interior surface to slidably engage the tapered outer surface of the gripping sleeve 32 so as to impart load thereto from a tension loading apparatus without introducing bending loads. The pulling sleeve 34 is configured for attachment to the tension loading apparatus via a loading cap 36. Associated with the loading cap 36 is an element 38 that extends longitudinally for engagement to the loading apparatus. The loading cap 36 is threadably engaged with the pulling sleeve 34 so as to provide load transfer therebetween. To minimize elastic rebound at failure, the gripping sleeve 32 is preloaded using a ring 40 and a plurality of fasteners 42 that are threadably engaged in the loading cap 36 and which extend therethrough to contact the ring 40. Advancing the fasteners 42 adjusts the preload imparted by the ring 40 on the gripping sleeve 32.

Figure 6:
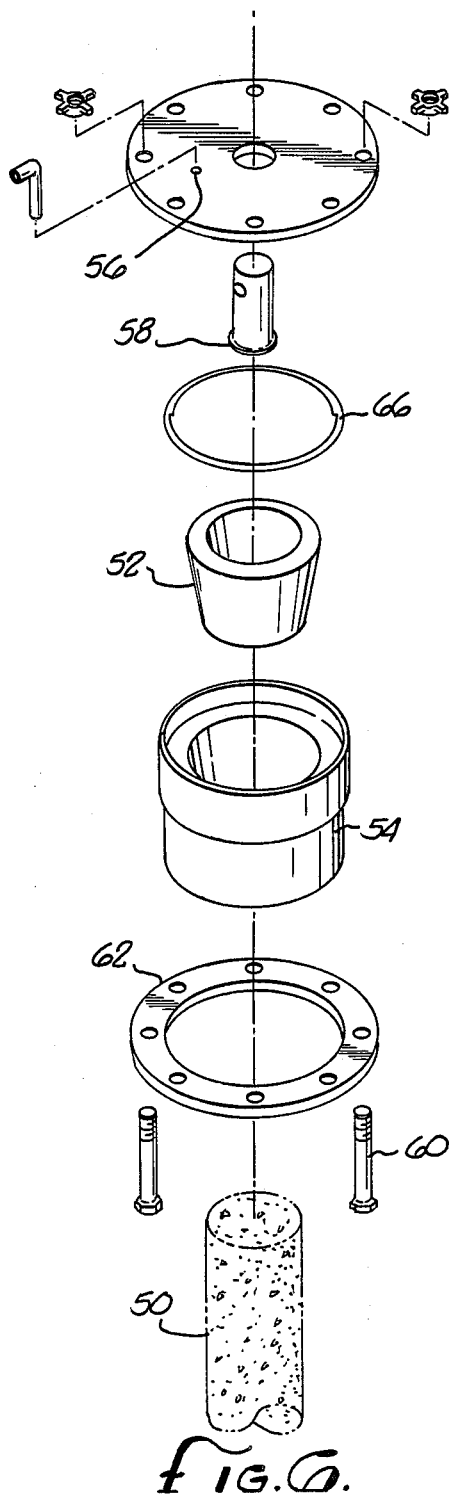
FIG. 6 is a exploded perspective view of the apparatus of FIG. 5 showing the constituent elements prior to assembly.

FIGS. 5 and 6 illustrate an apparatus for gripping a specimen 50. In this apparatus, the gripping sleeve 52 is similar to the gripping sleeve 32 previously discussed. The interior surface of the pulling sleeve 54 is likewise similar to that of the pulling sleeve 34, and the pulling sleeve 54 and gripping sleeve 52 impart load to the specimen 50 in the same manner as the pulling sleeve 34 and gripping sleeve 32, discussed above. However, whereas the loading cap 36 was threadably engaged with the pulling sleeve 34, the loading cap 56 is engaged with the pulling sleeve 54 by using a plurality of removable fasteners 60. The fasteners 60 are attached to the pulling sleeve 54 by means of a ring 62 mounted against an annular shoulder formed in the outer surface of the pulling sleeve 54. The ring 62 has a series of longitudinally oriented apertures adapted to receive the fasteners 60. The loading cap 56 is in turn provided with a plurality of longitudinally oriented apertures formed adjacent the edge thereof. The apertures on the ring 62 and the loading cap 56 are aligned in order to receive the fasteners 60. Wing nuts 64 are used to secure the fasteners 60 and permit load transfer between the loading cap 56 and pulling sleeve 54.

One end of the pulling sleeve 54 extends beyond the end of the specimen 50 and is configured to form a cylindrical recess that is adapted to slidably receive a corresponding portion of the loading cap 56. A resilient "O" ring 66 disposed within the cylindrical recess of the pulling sleeve 56 provides a sealed chamber 68 in conjunction with the loading cap 56, the pulling sleeve 54, the gripping sleeve 52 and the specimen 50. To minimize elastic rebound upon failure, a pressurized fluid such as air is introduced into the chamber 68 via a tubular insert 70 extending through an aperture in the loading cap 56.

Figure 8:
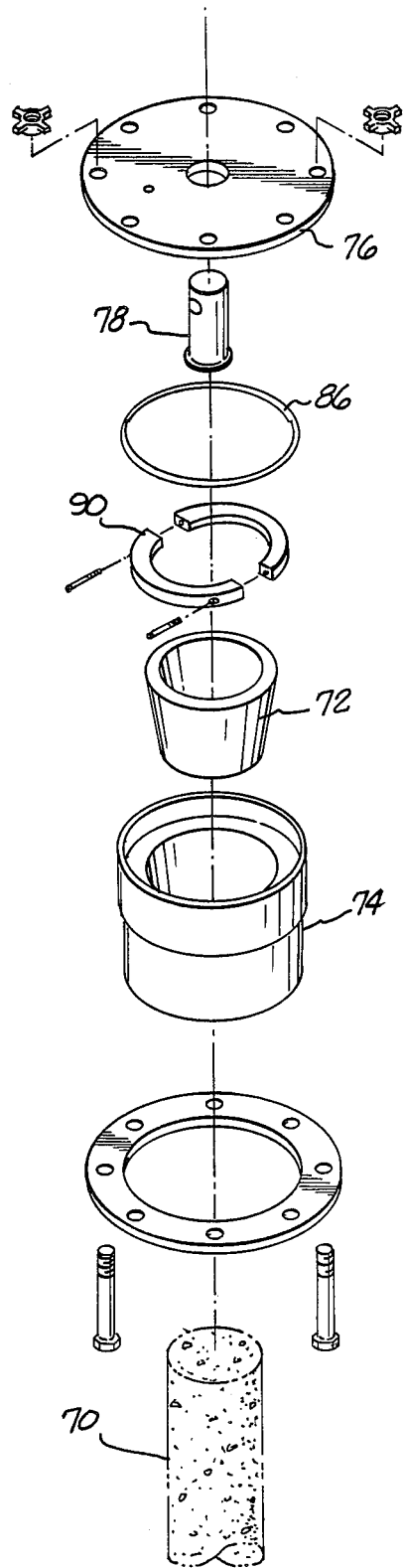
FIG. 8 is an exploded perspective view of the apparatus of FIG. 7 showing the constituent elements prior to assembly.

FIGS. 7 and 8 illustrate an apparatus for gripping a specimen 70. The apparatus includes a gripping sleeve 72, a pulling sleeve 74 and a loading cap 76. These elements function similarly to elements 52, 54 and 56, discussed above. The pulling sleeve 74 and loading cap 76 are attached together in the same manner as the pulling sleeve 54 and loading cap 56. In the apparatus of FIGS. 7 and 8, elastic rebound upon failure is minimized using a ring-shaped end piece 90 configured to fit over the cylindrical surface of the specimen 70. The end piece 90 is secured to the specimen 70 using threaded fasteners. It is positioned adjacent the gripping sleeve 72 so as to impart compressive forces on the gripping sleeve as the specimen is loaded.

To test the tensile strength of a brittle material, apparatus constructed in accordance with the present invention can be placed at each end of a specimen. As the specimen is loaded, the apparatus will self align at the tapered interface between the gripping and pulling sleeves and provide non-localized stress distribution over the surface of the specimen such that the specimen will fail at or near its true tensile strength value.

Thus, a device and method for tensile testing of brittle materials is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. An apparatus for testing cementitious materials in tension comprising a gripping sleeve of a viscous yieldable material, said sleeve being configured to surround a portion of a specimen of cementitious material and to grip the specimen, and a pulling sleeve adapted to engage said gripping sleeve and to impart a pulling load thereon.

2. A self-aligning apparatus for gripping a specimen of brittle material for tension loading comprising:
  a gripping sleeve of a viscous yieldable material, said sleeve having an inner surface adapted to grip a specimen and a tapered outer surface;
  a pulling sleeve for applying load to said gripping sleeve, said pulling sleeve having a tapered inner surface configured to engage the tapered outer surface of said gripping sleeve, said pulling sleeve being adapted for attachment to a tension loading apparatus; and
  means for minimizing elastic rebound.

3. The apparatus set forth in Claim 2 wherein said means for minimizing elastic rebound comprise an end piece secured to the specimen adjacent said gripping sleeve.

4. The apparatus set forth in Claim 2 wherein said means for minimizing elastic rebound comprise a pressurized fluid adjacent said gripping sleeve.

5. The apparatus set forth in Claim 2 wherein said means for minimizing elastic rebound comprise a ring member positioned against said gripping sleeve.

6. The apparatus set forth in claim 2 further including a loading cap, said cap providing attachment between said pulling sleeve and the tension testing apparatus.

7. The apparatus set forth in claim 6 wherein said means for minimizing elastic rebound comprise a ring member positioned against said gripping sleeve, and further including fasteners in threaded engagement with said cap, said fasteners being positioned to urge said ring member against said gripping sleeve.

8. The apparatus set forth in claim 6 wherein said means for minimizing elastic rebound comprise a pressurized fluid adjacent said gripping sleeve, said fluid being retained adjacent said gripping member in a chamber defined in part by said cap.

9. An apparatus for imparting a uniaxial load to a cylindrical specimen of brittle material comprising:
  a gripping sleeve of a viscous yieldable material, said sleeve having an inner surface adapted to fit over the specimen and an outer surface of frustoconical shape having an apex oriented toward the center of the specimen;
  a pulling sleeve for applying load to said gripping sleeve, said pulling sleeve having a frustoconical inner surface configured to engage the outer surface of said gripping sleeve;
  a loading cap attached to said pulling sleeve, said loading cap being configured for attachment to a tension loading device; and
  a ring secured about the specimen and bearing against the gripping sleeve, to minimize elastic rebound.

10. A method for testing brittle material in tension comprising the steps of:
  imparting a uniaxial tension load to a specimen of brittle material using an apparatus comprising:
  a gripping sleeve of a viscous yieldable material, said sleeve being adapted to grip the specimen;
  means for imparting load to said gripping sleeve; and
  means for minimizing elastic rebound.

11. An apparatus for applying tension to a specimen of brittle material comprising a gripping sleeve of a viscous yieldable material, said sleeve being adapted to grip the specimen and having a tapered outer surface, and means for applying load to said gripping sleeve.

12. An apparatus for applying tension to a specimen of brittle material comprising a gripping sleeve of a viscous yieldable material, said sleeve being adapted to grip the specimen, means for applying load to said gripping sleeve, and means for reducing elastic rebound.

13. An apparatus for applying tension to a specimen of brittle material comprising a gripping sleeve of a viscous yieldable material, said sleeve having an inner surface adapted to grip a specimen and a tapered outer surface, and a pulling sleeve for applying load to said gripping sleeve, said pulling sleeve having a tapered inner surface configured to engage the tapered outer surface of said gripping sleeve, said pulling sleeve being adapted for attachment to a tension loading apparatus.

14. An apparatus for applying tension to a specimen of brittle material comprising a gripping sleeve of a viscous yieldable material adapted to grip a test specimen and a pulling sleeve adapted to impart a pulling force to said gripping sleeve and a compressive force thereon that varies as a function of said pulling force.

15. An apparatus for applying tension to a cementitious material specimen comprising a gripping sleeve of a viscous yieldable material adapted to surround and grip a cementitious material specimen and a pulling sleeve adapted to engage said gripping sleeve and to impart pulling and compressive forces thereon.

* * * * *